United States Patent
Skoletsky

(10) Patent No.: US 11,696,694 B2
(45) Date of Patent: Jul. 11, 2023

(54) METHOD AND DEVICE FOR CALIBRATION OF A CAPILLARY BLOOD FLOW METER

(71) Applicant: Dermaflow LLC, Moorestown, NJ (US)

(72) Inventor: Ilya Skoletsky, Beer Sheva (IL)

(73) Assignee: Dermaflow LLC, Moorestown, NJ (US)

( * ) Notice: Subject to any disclaimer, the term of this patent is extended or adjusted under 35 U.S.C. 154(b) by 639 days.

(21) Appl. No.: 16/634,345

(22) PCT Filed: Jul. 30, 2018

(86) PCT No.: PCT/US2018/044369
§ 371 (c)(1),
(2) Date: Jan. 27, 2020

(87) PCT Pub. No.: WO2019/027895
PCT Pub. Date: Feb. 7, 2019

(65) Prior Publication Data
US 2021/0085192 A1    Mar. 25, 2021

Related U.S. Application Data

(60) Provisional application No. 62/538,734, filed on Jul. 30, 2017.

(51) Int. Cl.
*A61B 5/026* (2006.01)
(52) U.S. Cl.
CPC ...... *A61B 5/026* (2013.01); *A61B 2560/0223* (2013.01); *A61B 2560/0242* (2013.01)

(58) Field of Classification Search
CPC ............. A61B 5/026; A61B 2560/0223–0228; A61B 2560/0238; A61B 5/1495; G01F 1/698
See application file for complete search history.

(56) References Cited

U.S. PATENT DOCUMENTS 4,786,394 A    11/1988   Enzer et al.
5,050,613 A    9/1991    Newman et al.
(Continued)

FOREIGN PATENT DOCUMENTS

EP    2243425 A2    10/2010

OTHER PUBLICATIONS

Toumi et al. "Design and validation of an ambulatory system for the measurement of the microcirculation in the capillaries: microHematron device." Annu Int Conf IEEE Eng Med Biol Soc. 2009;2009:4120-3. (Year: 2009).*

(Continued)

*Primary Examiner* — Meredith Weare
(74) *Attorney, Agent, or Firm* — Eversheds Sutherland (US) LLP

(57) ABSTRACT

In an aspect, this disclosure relates to methods and devices for calibration of capillary blood flow meters for measuring capillary blood flow in absolute flow units (such as mL/min× 100 g of tissue). For example, the calibration method utilizes the combination of a wet model device and a dry model device to provide a convenience, easy-to-use, and accurate calibration and measurement in absolute flow units. In an aspect, the dry model device can use thermal conductivity parameters from the wet model device, which can be translated into thermal conductivity parameters in a dry model device, which can be used to calibrate the capillary blood flow meter in absolute units.

26 Claims, 6 Drawing Sheets

(56) References Cited

U.S. PATENT DOCUMENTS

| | | | | |
|---|---|---|---|---|
| 5,205,293 | A * | 4/1993 | Ito | A61B 5/0265 600/549 |
| 6,221,025 | B1 * | 4/2001 | Skoletsky | A61B 5/026 600/549 |
| 6,488,623 | B1 * | 12/2002 | Ozarowski | A61B 5/026 600/363 |
| 2003/0233860 | A1 * | 12/2003 | Deane | G01F 1/668 73/1.16 |
| 2010/0016689 | A1 * | 1/2010 | Kanayama | A61B 5/6843 600/316 |
| 2013/0041234 | A1 | 2/2013 | Grinstein et al. | |
| 2015/0018655 | A1 | 1/2015 | Buse et al. | |

OTHER PUBLICATIONS

International Search Report and Written Opinion, PCT/US18/044369, 14 pages, dated Oct. 24, 2018.

* cited by examiner

METHOD AND DEVICE FOR CALIBRATION OF A CAPILLARY BLOOD FLOW METER

CROSS REFERENCE TO RELATED APPLICATIONS

This application is a 35 U.S.C. § 371 National stage application of International Patent Application No. PCT/US2018/044369, filed Jul. 30, 2018, which claims the benefit of priority to U.S. Provisional Patent Application No. 62/538,734, filed Jul. 30, 2017, each of which is incorporated herein by reference in its entirety.

TECHNICAL FIELD

This disclosure relates to non-invasive methods and devices for skin blood flow measurements and methods for calibrating such devices.

BACKGROUND OF THE INVENTION

Measuring skin blood flow, also referred to as capillary blood flow, is important in various medical applications such as obtaining information about skin function, treating burns or skin ulcers, applying skin grafts, or evaluating peripheral hemodynamics Non-invasive methods of monitoring skin blood flow include plethysmography, laser-Doppler flowmeter methods, and thermal clearance methods.

Thermal methods of measuring skin blood flow non-invasively include locally heating an area of skin and measuring a temperature difference along the surface of the skin. The heated area can be cooled by a variety of heat transfer mechanisms, such as conduction through and along the skin and convection by the skin blood flow. Variables such as heating or cooling power, the temperature difference, and heat exchange mechanisms can be used in heat transfer equations to calculate the blood flow.

Current thermal devices use a disk-shaped sensor that includes a centrally located heating and measuring element and a peripherally located reference measuring element. Under current methodologies which use disposable sensors, each time a sensor is replaced it is necessary to recalibrate the new sensor with the capillary blood flow meter. Recalibration requires considerable effort and time using unwieldy and expensive fluid flow equipment of a "wet model" calibration device. In addition to its inconvenience, the fluid flow in current wet model devices does not accurately reflect the real structure of blood flow in the capillaries and thus cannot provide calibration of disposable and/or reusable capillary blood flow sensors in absolute units, the latter characteristics being well-accepted as state of the art for other known, routine parameters and measurements, whether in the clinic or in the home.

Therefore, new devices are needed as well as methods and apparatuses which are convenient and easy to use, and which allow rapid, routine, and accurate calibration of inexpensive and disposable sensors as well as reusable sensors for a capillary blood flow meter. New methods and devices are also needed for measuring capillary blood in absolute flow units and for calibrating a capillary blood flow apparatus in absolute flow units.

BRIEF SUMMARY OF THE INVENTION

This disclosure describes methods and devices for calibrating thermal capillary blood flow systems to provide accurate skin blood flow measurements in absolute rate values, such as milliliters per minute per 100 grams of tissue (mL/min×100 g of tissue). Specifically, this disclosure describes methods for calibrating a capillary blood flow apparatus in absolute flow units, methods for measuring capillary blood flow in absolute flow units, and devices for measuring capillary blood in absolute flow units. This disclosure also discloses an improved wet model system or device for use with the methods described herein.

In an aspect, there are provided a method and device for calibration of a capillary blood flow meter, which utilizes a capillary blood flow sensor or sensor module and a calibrating unit in combination with the capillary blood flow meter. Calibration is carried out with the capillary blood flow sensor by using reference systems of devices including a capillary blood flow wet model device and a capillary blood flow dry model device. The methodology disclosed herein takes into account a new design for a wet model device which emphasizes accuracy of the blood flow parameter, which is then used to transfer these features to a dry model device and calibrating unit. Specifically, the dry model device disclosed herein employs heater power parameters of the capillary blood flow meter obtained using the wet model device and translates these power parameters to thermal conductivity parameters in the dry model device, which permits rapid calibration of the capillary blood flow meter in absolute units. This use in series of two reference systems and devices facilitates commercialization of a compact and inexpensive capillary blood flow device that can make routine measurements of capillary blood flow in absolute units such as mL/min×100 g of tissue (milliliters per minute per 100 grams of tissue).

According to an aspect of the disclosure, there is provided a method for calibrating a capillary blood flow sensor in absolute flow units, in which the method can comprise:

a) providing a capillary blood flow sensor comprising [1] a heater for changing the temperature of an area of a surface from a first temperature to a second temperature and for maintaining a constant temperature gradient between the first and second temperatures, and a power source for providing a power to the heater, and [2] a temperature sensor for measuring temperature at the area of the surface;

b) providing a wet model device comprising a flow path for a flowing fluid which is maintained at physiological temperature, one portion of which is covered by a barrier material having a top surface and a bottom surface and in contact with the flowing fluid on the bottom surface, and having a sufficient area for the heater and the temperature sensor to simultaneously contact the top surface of the barrier material;

c) [1] initiating a preselected first fluid flow along the flow path and determining a corresponding first heater power dissipation in order to maintain the temperature gradient constant and [2] initiating a preselected second fluid flow along the flow path and determining a corresponding second heater power dissipation in order to maintain the same constant temperature gradient;

d) providing a dry model device comprising a first site on a first heat sink and a second site on a second heat sink and translating the first heater power dissipation and the second heater power dissipation of the wet model device to the thermal conductivity parameters at the first site and at the second site by [1] adjusting the thermal conductivity at the first site when the heater is operated at the first power determined using the wet model device, to maintain the temperature gradient constant, and [2] adjusting the thermal conductivity at the second site when the heater is operated at the second heater power determined using the wet model device, to maintain the temperature gradient constant; and e) calibrating a capillary blood flow sensor module in absolute flow units using the dry model device by assigning the first heater power to correspond to the preselected first fluid flow and assigning the second heater power to correspond to the preselected second fluid flow.

In further aspects of the disclosure, there is provided a process for calibrating a capillary blood flow sensor in absolute flow units, in which the process can comprise:

a) contacting a capillary blood flow sensor with a first site on a first heat sink of a dry model device, wherein the capillary blood flow sensor comprises a heater and a temperature sensor; b) activating a control signal (b) to measure a first temperature of the first site, then deactivating the control signal (b);

c) activating a control signal (a) to turn ON the heater for a predetermined time period to heat the sensor on the first site to a second temperature, wherein the temperature gradient between the first temperature and the second temperature is maintained constant at +x° C.;

d) activating a control signal (c) to measure the heater power required to maintain the temperature gradient constant;

e) activating a control signal (d) to turn ON a calibrating unit and converting the heater power dissipation to a measured flow rate based upon the dry model device;

f) comparing the measured flow rate based upon the dry model device to a first absolute flow rate based upon a wet model device;

g) adjusting the number of layers or the thickness of a material on the first site of the dry model device to reduce the difference between the measured flow rate and the first absolute flow rate;

h) repeating steps f) and g) as needed until the difference between the measured flow rate based upon the dry model device and the first absolute flow rate based upon the wet model device is 0; and i) repeating steps a) through h) by contacting the capillary blood flow sensor with a second site on a second heat sink of the dry model device, and comparing the measured flow rate based upon the dry model device to a second absolute flow rate based upon the wet model device and adjusting the number of layers or the thickness of a material on the second site of the second heat sink of the dry model device until the difference between the measured flow rate based upon the dry model device and the second absolute flow rate based upon the wet model device is 0.

This disclosure also provides a method for measuring capillary blood flow in absolute flow units, in which the method can comprise:

a) providing a capillary blood flow sensor comprising [1] a heater for applying heat to an area of skin to change the temperature of the skin from a first temperature to a second temperature and for maintaining a constant temperature gradient between the first and second temperatures, and a power source for providing a power to the heater, and [2] a temperature sensor for measuring temperature at the area of skin;

b) with the temperature sensor, measuring the first temperature at the area of skin;

c) with the heater, applying heat to the area of skin to change the first temperature to a second temperature and maintaining the temperature gradient constant;

d) measuring the heater power required to maintain the temperature gradient constant; and e) determining a capillary blood flow in absolute flow units by comparing the heater power dissipation with a linear relationship based upon the Fourier equation of flow;

wherein the capillary blood flow sensor is calibrated by:

f) providing a wet model device comprising a flow path for a flowing fluid which is maintained at physiological temperature, one portion of which is covered by a barrier material having a top surface and a bottom surface and in contact with the flowing fluid on the bottom surface, and having a sufficient area for the heater and the temperature sensor to simultaneously contact the top surface of the barrier material;

g) [1] initiating a preselected first fluid flow along the flow path and determining a corresponding first heater power in order to maintain the temperature gradient constant and [2] initiating a preselected second fluid flow along the flow path and determining a corresponding second heater power in order to maintain the temperature gradient constant;

h) providing the dry model device comprising a first site on a first heat sink and a second site on a second heat sink and translating the first heater power and the second heater power of the wet model device to the thermal conductivity parameters at the first site and at the second site by [1] adjusting the thermal conductivity at the first site when the heater is operated at the first heater power determined using the wet model device, to maintain the temperature gradient constant, and [2] adjusting the thermal conductivity at the second site when the heater is operated at the second heater power determined using the wet model device, to maintain the temperature gradient constant; and i) calibrating a capillary blood flow sensor in absolute flow units using the dry model device by assigning the first heater power to correspond to the preselected first fluid flow and assigning the second heater power to correspond to the preselected second fluid flow.

In still further aspects, this disclosure describes a process for measuring a capillary blood flow on a subject in absolute flow units, the process comprising:

a) contacting a capillary blood flow sensor with an area of skin of a subject, wherein the capillary blood flow sensor comprises a heater and a temperature sensor;

b) activating a control signal (b) to measure a first temperature of the skin, then deactivating the control signal (b);

c) activating a control signal (a) to turn ON the heater for a predetermined time period to heat the area of the skin to a second temperature, wherein the temperature gradient between the first temperature and the second temperature is maintained constant at +x° C.;

d) activating a control signal (c) to measure the heater power required to maintain the temperature gradient constant; and e) converting the heater power dissipation to the capillary blood flow in absolute flow units.

In further aspects, this disclosure also provides a device for measuring capillary blood flow in absolute flow units, in which the device can comprise:

a) a heater for applying heat to an area of skin to change the temperature of the skin from a first temperature to a second temperature and for maintaining a constant temperature gradient between the first and second temperatures, and a power source for providing power to the heater;

b) a temperature sensor for measuring temperature at the area of skin;

c) a controller in communication with the heater and the temperature sensor which [1] operates the heater for maintaining the temperature gradient constant and [2] operates the temperature sensor in a first operative mode and a second operative mode, wherein in the first operative mode the temperature sensor measures the first temperature at the area of skin, and wherein in the second operative mode, the controller operates the heater to maintain the temperature gradient constant between the first and second temperatures;

d) a processor in communication with the controller for determining a capillary blood flow in absolute flow units corresponding to the measured first temperature and the heater power required to maintain the temperature gradient constant; and e) a calibrating unit in communication with the processor which has been standardized in absolute flow units by: [1] in a wet model device, determining a first heater power dissipation corresponding to a preselected first fluid flow and determining a second heater power dissipation corresponding to a preselected second fluid flow, each in order to maintain the temperature gradient constant; [2] in a dry model device, adjusting the thermal conductivity of one or more layers at a first site on a first heat sink when the heater is operated at the first heater power obtained using the wet model device to obtain the constant temperature gradient at the preselected first fluid flow, and adjusting the thermal conductivity of one or more layers at a second site on a second heat sink when the heater is operated at the second power obtained using the wet model device to correspond to the constant temperature gradient at the preselected second fluid flow; and [3] standardizing the calibrating unit in absolute flow units using the dry model device by assigning the first heater power to correspond to the preselected first fluid flow and assigning the second heater power to correspond to the preselected second fluid flow.

These and other aspects and embodiments of the disclosure are set out in the figures, examples, and detailed description below. Additional features or variations thereof can be provided in addition to those set forth herein, such as for example, various feature combinations and sub-combinations of these described in the detailed description.

DETAILED DESCRIPTION

Figure 1:
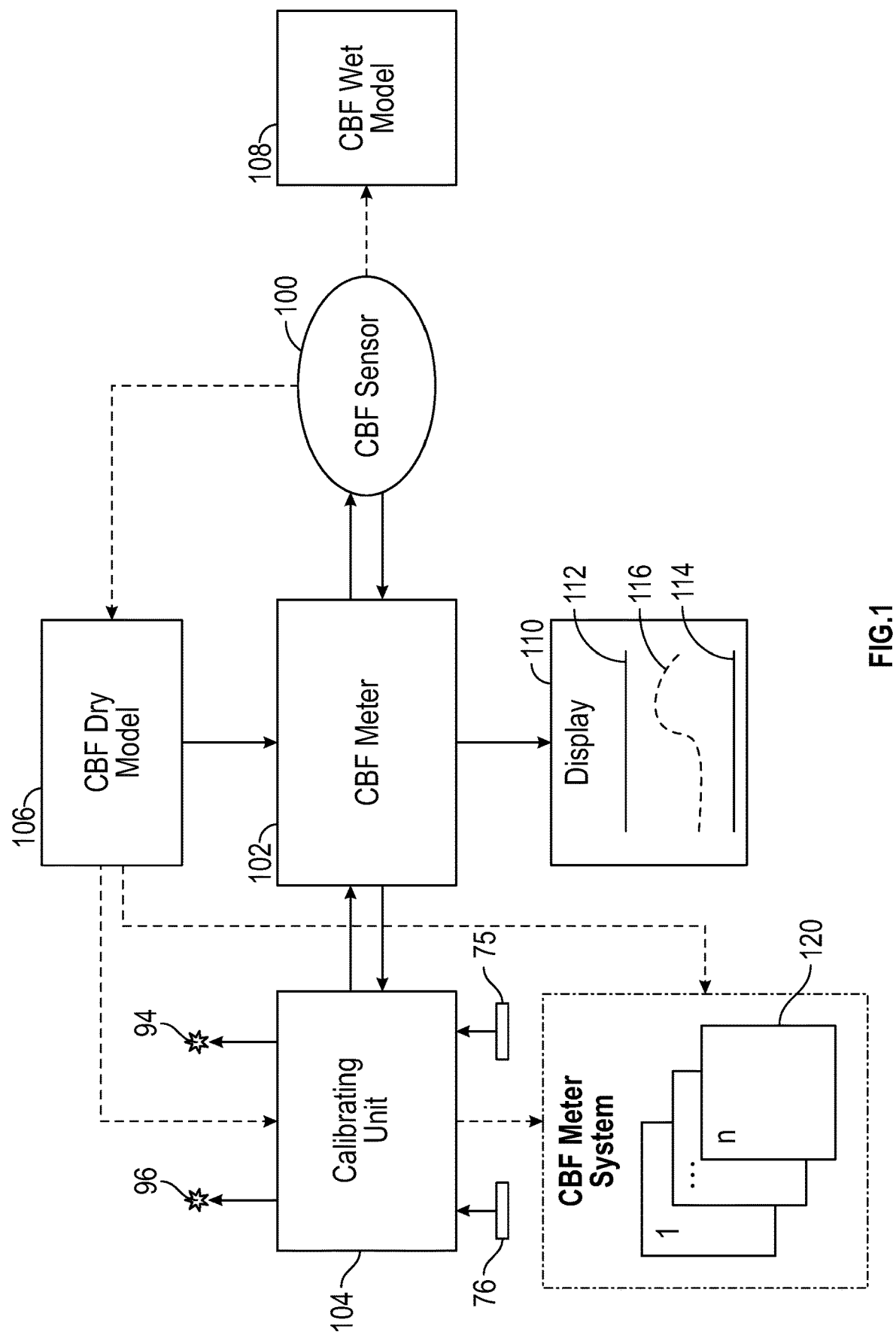
FIG. 1 provides a conceptual illustration of exemplary components of the capillary blood flow meter and the inter-communications of the various components and units which allow the calibration of a capillary blood flow meter in absolute flow units.

According to aspects of this disclosure, provided herein are: devices and methods for calibrating a capillary blood flow apparatus in absolute flow units to provide accurate skin blood flow measurements; devices and methods for accurately measuring capillary blood flow in absolute flow units; an improved wet model device for use with the capillary blood flow devices and methods described herein; and a new dry model device in which thermal conductivity and liquid flow parameters obtained using the wet model device can be integrated or incorporated. The disclosed physiological measurements are provided by improved and convenient methodologies and devices which enable capillary blood flow to be measured in absolute flow units on a routine and convenient basis.

Devices and methods for the calibration of sensors for capillary blood flow (CBF) measurements which use the principles of fluid flow in a wet model type system include those reported in U.S. Pat. No. 5,205,293 and in D. Toumi, C. Gehin, A. Dittmar, E. McAdams, Hematron device, 31st Annual International Conference of the IEEE EMBS, Minneapolis, Minn., USA, Sep. 2-6, 2009 (Toumi et al.). A capillary blood flow device and sensor has been previously described by this inventor in U.S. Pat. No. 6,221,025. These references are incorporated herein by reference in their entireties. Generally, wet (or dry) model calibration systems are referred to herein as wet (or dry) model devices.

In some aspects, this disclosure provides methods, devices and system for the accurate capillary blood flow calibration using an improved wet model device, which allows calibration in absolute units. In other aspects, this disclosure provides for a calibrating unit as part of the capillary blood flow measuring device which is an inexpensive and compact capillary blood flow dry model device, which can be used in daily and routine measurements and monitoring. Specifically, the dry model device disclosed herein employs thermal conductivity parameters from the wet model device and translates them to thermal conductivity parameters of the dry model device which can be used to calibrate the capillary blood flow meter in absolute units. This unique calibration method which utilizes the combination of a wet model device and a dry model device provides certain advantages such as convenience and ease of calibration, as well as measurement in absolute flow units.

Definitions. To define more clearly the terms used herein, the following definitions are provided, and unless otherwise indicated, the following definitions are applicable to this disclosure. If a term is used in this disclosure but is not specifically defined herein, the definition from the *Academic Press Dictionary of Science and Technology*, ed. C. Morris, Academic Press, Inc.; San Diego, c. 1992, can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

While devices and methods are described in terms of "comprising" various components or steps, the compositions and methods can also "consist essentially of" or "consist of" the various components or steps, unless stated otherwise. The terms "including", "with", and "having", as used herein, are defined as comprising (i.e., open language), unless specified otherwise.

The terms "wet model" and "dry model" as used herein refer to the devices that are used in the calibration of the capillary blood flow sensor. Therefore, these terms are also referred to as a "wet model device" and a "dry model device", respectively. The wet model device uses thermal conductivity measurements of a flowing liquid, whereas the dry model device uses thermal conductivity measurements of a solid material.

The term "capillary blood flow sensor" refers to the combination of [1] a heater or heating means for heating a surface or an area of a surface, including skin, and for applying and maintaining a constant predetermined temperature gradient, and [2] a temperature sensor or temperature sensing element for measuring temperature, whether this combination is physically attached or not. When the combination of a heater and a temperature sensor are physically combined or attached into a single unit, the single unit can be referred to as a "capillary blood flow sensor module" or simply, "sensor module." Typically, the heater and the temperature sensor are combined into a single, thermally insulated capillary blood flow sensor module, which can be thermally insulated on the portions of the sensor module unit that are not in contact with the skin or the surface to be heated and measured. In this disclosure, reference to a "sensor" or a "sensor module" can include the other, unless the context requires otherwise.

Regarding the "sensor" and the "sensor module" of this disclosure, the sensor and sensor module can further include other elements in addition to the heater and temperature sensor for measuring various parameters at the skin, for providing various stimuli to the skin, or for carrying out any number of other functions. This is particularly useful in the sensor module, which if desired can further include, for example, an accelerometer, a heart rate sensor, an oxygen saturation or blood oxygen sensor, a blood pressure sensor, and the like, including any combinations thereof. In this manner, the sensor module provides a convenient way of measuring several parameters while in contact with the skin.

Terms such as "controller", "processor", "calibrating unit", and the like, refer to the electronic means by which the various functions of the devices and methods disclosed herein are carried out. The controller, processor, calibrating unit, and the like, can be combined into a single device or computer, or they can be separated into individual electronic devices or sub-combinations of electronic devices, as well understood by the person of ordinary skill in the relevant art. The controller is the structure that functions to control, the processor is the structure that carries out the processing function, and the calibrating unit is the structure that carries out the calibration function, and these structures can be the same or can be different. These may also be referred to herein as a control means, a processing means, and a calibrating means.

The term "capillary blood flow meter" refers to the combination, whether physically integrated or not, of the electronic means by which the various functions of the devices and methods disclosed herein are carried out. For example, the "capillary blood flow meter" can include the "controller" and "processor" and associated software. Generally, the "capillary blood flow meter" can include the computer that controls heater and measurement functions at various times and in various sequences, and further can include the processor that runs calculations to, for example, convert heater power to blood flow. By referring to the calibration of a "capillary blood flow sensor", it is intended to also refer to the calibration of the "capillary blood flow meter", as "calibration" involves both the computational means as well as the heating and temperature measurement means.

The term "heat sink" can be used to refer to a solid heat conductive material, such as a non-ferrous metal, having a very high heat conductivity, on which are located one or more "sites" or "placement sites" for location of the capillary blood flow sensor module in the dry model device. For example, in some embodiments, the dry model device can include a first site (first placement site) and a second site (second placement site) that are situated on a single, contiguous heat sink material such as a metal, such as illustrate in FIG. 4A. In other aspects, the dry model device can include a first site (first placement site) which is located on a first heat sink and a second site (second placement site) which is located on a second heat sink, in which the first and second heat sinks are either [1] individual and physically separated (non-contiguous or non-continuous) heat sink materials, or [2] thermally insulated from each other, an example of which is illustrated in FIG. 4B. Unless specified otherwise, or unless the context requires otherwise, by claiming a first site on a first heat sink and a second site on second heat sink, it is intended to capture all of these embodiments, including those in which first heat sink and second heat sink are combined into a single, contiguous heat sink material, and also to capture those embodiments in which the first and second heat sinks are physically and/or thermally separated from each other.

The term "physiological temperature" it is intended to reflect any physiological temperature for mammals, that is, this device can be used in any mammal and adjusted according to that mammal's normal physiological temperature. Typically, the methods and devices disclosed herein are used with human subjects, for which an approximate average temperature for healthy adults is about 37.0° C.

Numerical ranges are disclosed herein. When a range of any type is disclosed or claimed, Applicant's intent is to disclose or claim individually each possible number that such a range could reasonably encompass, including end points of the range as well as any sub-ranges and combinations of sub-ranges encompassed therein, unless otherwise specified. For example, by disclosing a temperature of from 30° C. to 40° C., Applicant's intent is to recite individually, 30° C., 31° C., 32° C., 33° C., 34° C., 35° C., 36° C., 37° C., 38° C., 39° C., and 40° C., including any sub-ranges and combinations of sub-ranges encompassed therein, and these methods of describing such ranges are interchangeable. Moreover, all numerical end points of ranges disclosed herein are approximate, unless excluded by proviso. As a representative example, if a temperature is disclosed in a range of from 30° C. to 40° C., this range should be interpreted as encompassing temperatures in a range from "about" 30° C. to "about" 40° C. Applicant reserves the right to proviso out or exclude any individual members of any such group of values or ranges, including any sub-ranges or combinations of sub-ranges within the group, that can be claimed according to a range or in any similar manner, if for any reason Applicants choose to claim less than the full measure of the disclosure, for example, to account for a reference that Applicants can be unaware of at the time of the filing of the application.

Values or ranges may be expressed herein as "about" a particular value. When such values or ranges are expressed, other embodiments disclosed include the specific value recited. Similarly, when values are expressed as approximations, by use of the antecedent "about," it will be understood that the particular value forms another embodiment. In another aspect, use of the term "about" can mean±20% of the stated value, ±15% of the stated value, ±10% of the stated value, ±5% of the stated value, or ±3% of the stated value.

All publications and patents mentioned herein are incorporated herein by reference for the purpose of describing and disclosing, for example, the constructs and methodologies which can be used in connection with the presently described devices and methods. The publications discussed throughout the text are provided solely for their disclosure prior to the filing date of the present application. Nothing herein is to be construed as an admission that the inventors are not entitled to antedate such references.

In an aspect, this disclosure provides a novel methodology to enable routine measurements of capillary blood flow, which may also be referred to in this disclosure and in the technical literature as skin, dermal, peripheral and/or microcirculation flow, in which calibration of the measurement device provides capillary blood flow in absolute flow units.

Figure 2:
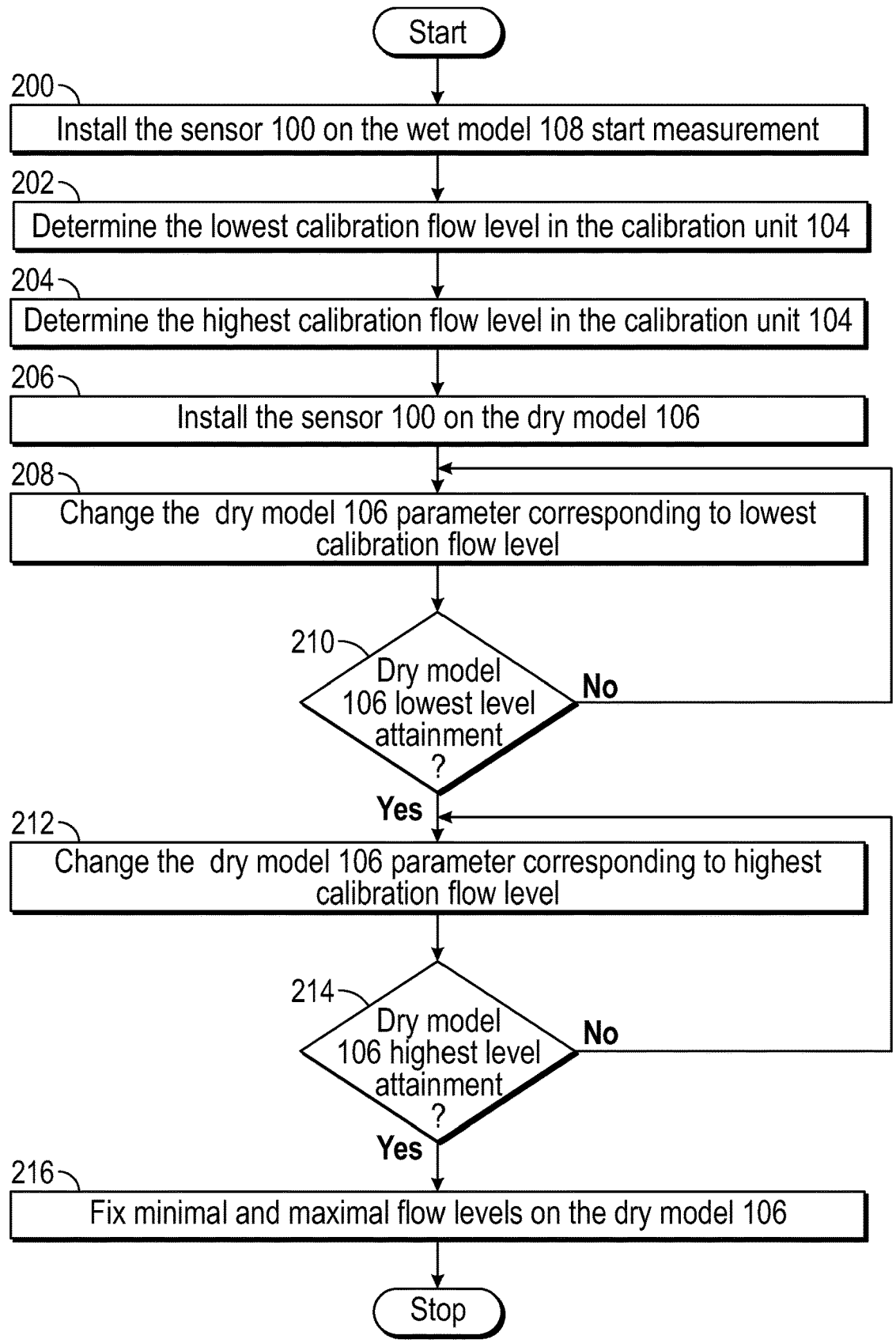
FIG. 2 illustrates a sequence for the functioning of the main components, units, and devices presented on FIG. 1, including how the dry model device references a wet model device to allow rapid and convenient calibration of a capillary blood flow meter in absolute flow units.

FIG. 1 provides a conceptual illustration of exemplary components of the capillary blood flow meter and the inter-communications of the various components and units which allow the calibration of a capillary blood flow meter in absolute flow units. The concept illustrated in FIG. 1 is considered alongside FIG. 2, which illustrates a sequence for the functioning of the main components, units, and devices presented on FIG. 1. Among other things, FIG. 2 illustrates how the dry model device references a wet model device to allow rapid and convenient calibration of a capillary blood flow meter in absolute flow units.

In FIG. 1, capillary blood flow sensor 100 is illustrated together with a capillary blood flow meter 102 and monitor or display 110, wherein the capillary blood flow meter 102 can correspond, for example, to the capillary blood flow meter presented in U.S. Pat. No. 6,221,025, which provides a continuous measurement of capillary blood flow in relative units. In the capillary blood flow meter of U.S. Pat. No. 6,221,025, the measurement of capillary blood flow was associated with the measurement of heat conductivity of thin films by a thermal method, which is based on the Fourier equation as described below. While the capillary blood flow meter of U.S. Pat. No. 6,221,025 measured changes in capillary blood flow in relative units, this disclosure provides for measuring capillary blood flow in absolute units with the capillary blood flow meter of U.S. Pat. No. 6,221,025 or with any other thermal capillary blood flow meter.

Figure 5:
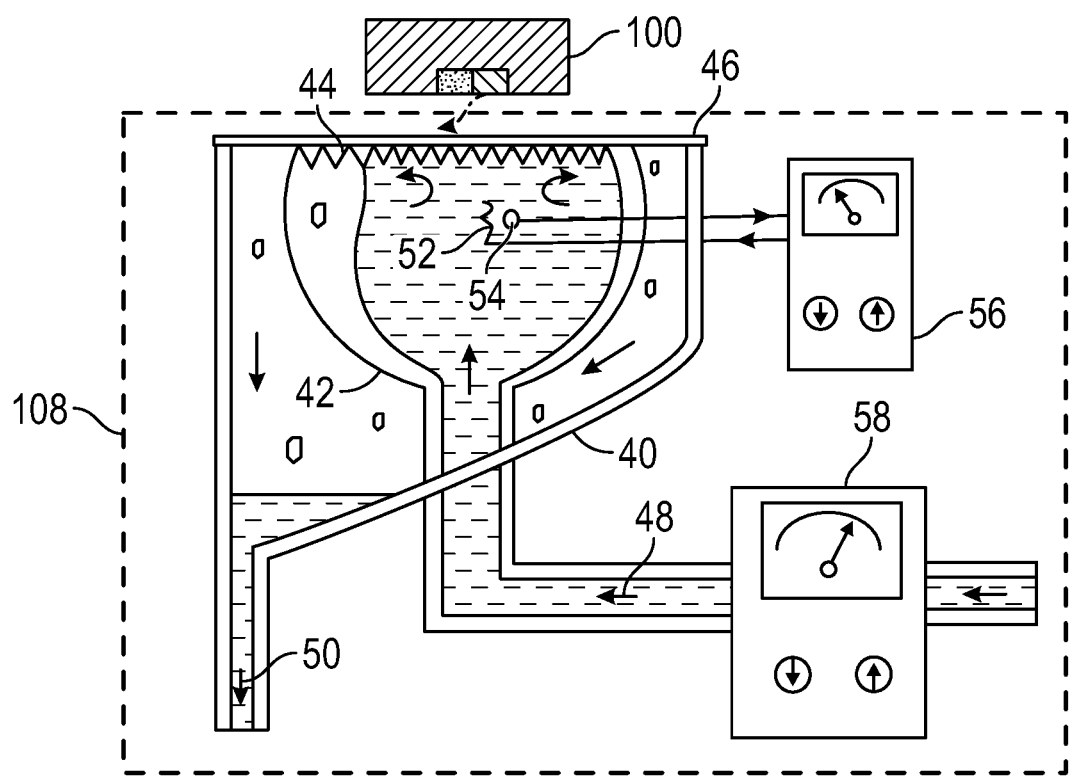
FIG. 5 provides a cross-sectional illustration of the new design of an accurate capillary blood flow wet model device, which is described in detail here. The upright internal fluid feeding tube and the external receiving tube, which allow determination of the thermal conductivity parameter of a preselected fluid flow, are specifically illustrated.

Calibration using the wet model device. The capillary blood flow parameter is calibrated in actual (absolute) units by calibrating the device and method to the value of an actual fluid flow provided in a "wet model" type calibration system, see 108 (FIG. 1 and FIG. 5). Various wet model devices have been described (see U.S. Pat. No. 5,205,293 and Toumi, et al.). The wet model device of the present disclosure is designed in a manner that more closely reflects the actual capillary blood flow, and as such, can be used for calibrating thermal capillary blood flow sensors of various designs to provide accurate capillary blood flow in absolute units. Specifically, this new wet model takes into account the actual human capillary blood flow range in absolute units of about 1-5 mL/min×100 g of tissue at the low end to about 50-100 mL/min×100 g of tissue (milliliters per minute per 100 grams of tissue) at the high end.

Various aspects of the wet model device 108 according to this disclosure and the use of the wet model device to calibrate capillary blood flow measurements in absolute units are described. Referring to FIG. 1 and FIG. 2, the capillary blood flow sensor 100, which also connects to the capillary blood flow meter 102 is installed on the capillary blood flow wet model device 108 and the mode of the continuous measurement is initiated, as represented by step 200 of FIG. 2. The device and method can use a monitor or display 110 for a visual display of the capillary blood flow data in real time. In an aspect, the structure of the wet model device is illustrated in FIG. 5 and described in detail herein below.

Figure 6:
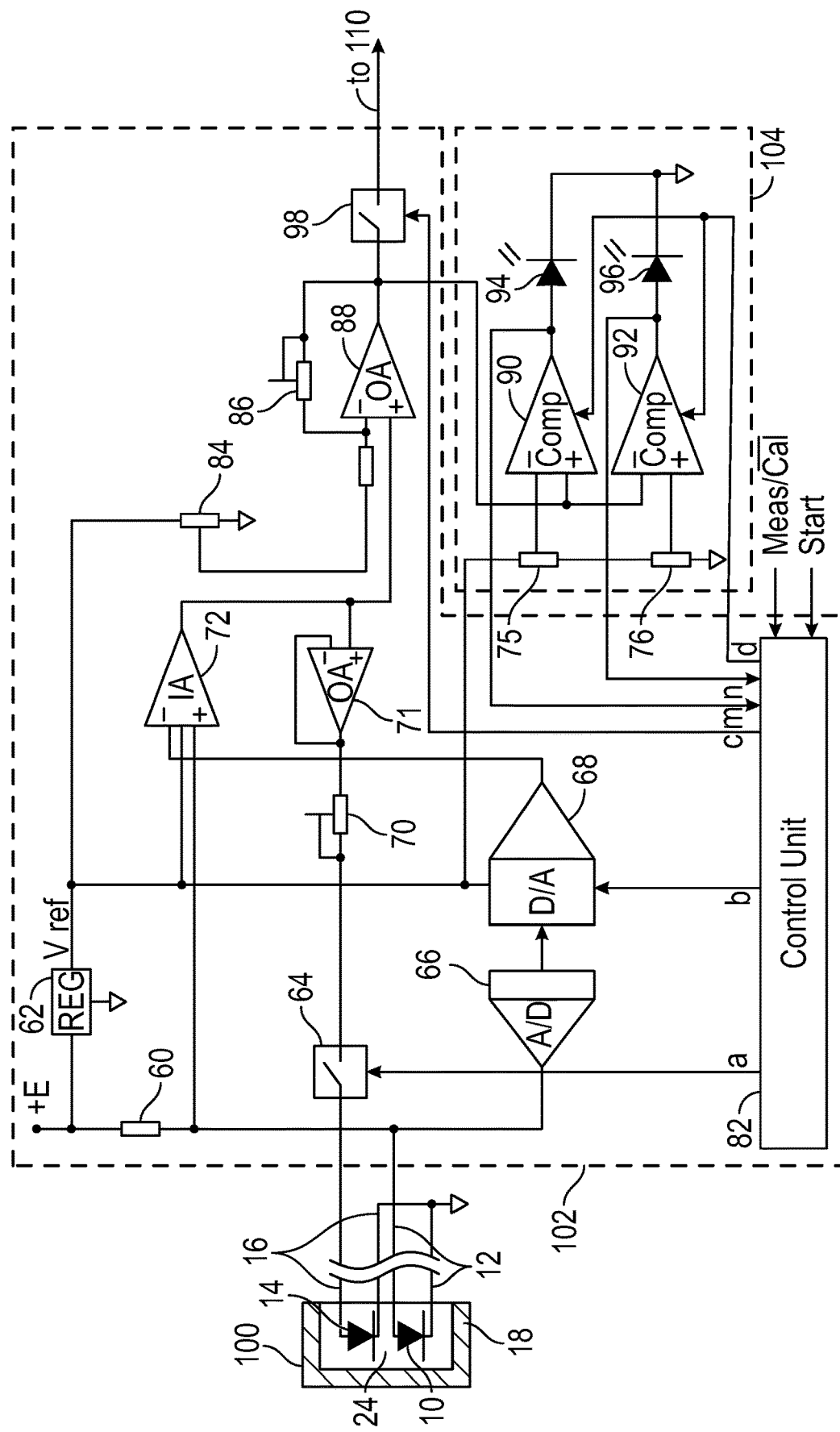
FIG. 6 illustrates a schematic block diagram of the structure of the capillary blood flow meter according to U.S. Pat. No. 6,221,025, which further includes an additional calibrating unit according to the present disclosure, which is constructed and operative in accordance with the present disclosure, with both temperature sensing apparatus and heating apparatus being constituted by silicon diodes.

Reference is also made to FIG. 6, which illustrates a schematic block diagram of the capillary blood flow meter according to U.S. Pat. No. 6,221,025, which further includes an additional calibrating unit according to the present disclosure. Although the calibrating unit 104 of FIG. 6 is illustrated with the specific capillary blood flow meter according to U.S. Pat. No. 6,221,025, calibrating unit 104 which is constructed and operative in accordance with the present disclosure can be used with any thermal capillary blood flow device.

The capillary blood flow wet model device 108 (see FIG. 1 and FIG. 5) fluid flow is adjusted to correspond to the actual physiological capillary blood flow values 116 which are designated by the measurement scale. Two adjustments are made: [1] a first to calibrate a first blood flow level that corresponds to a blood flow expected to be near the minimum of measured blood flows; and [2] a second to calibrate a second blood flow level that corresponds to a blood flow expected to be near the maximum of measured blood flows. This second adjustment uses the potentiometer 84 and variable resistor 86 of the operational amplifier 88, which correspond to the parameters V and P according to equation (2), and then adjusts the relevant potentiometers 75 and 76 of the calibration unit 104 in FIG. 6. That is, prior to using potentiometers 75 and 76, this method uses potentiometer 84 and variable resistor 86, which establishes the parameter of amplification of the range. These first and second measured blood flows may be referred to herein as the minimum and maximum blood flows. For example, the wet model device 108 can be adjusted to correspond to the human capillary blood flow range in absolute units of from about 5 to about 50 mL/min×100 g of tissue. The minimum blood flow value 114 (FIG. 1) can be set on the capillary blood flow wet model device 108 by setting potentiometer 76 (FIG. 6), which is incorporated into the calibration unit 104, until a minimum fluid flow value 114 is attained, for example, 5 mL/min×100 g of tissue. In an aspect, attaining the minimum flow value 114 with the relevant potentiometer setting can be indicated by, for example, an LED indicator 96, which can light when the potentiometer 76 reaches the desired value. This determination step is represented by step 202 of FIG. 2.

Similarly, the maximum blood flow value 112 (FIG. 1) for calibration purposes can be set on the capillary blood flow wet model device 108 by setting potentiometer 75 (FIG. 6), which is incorporated into the calibration unit 104, until a maximum fluid flow value 112 is attained, for example, 50 mL/min×100 g of tissue, 60 mL/min×100 g of tissue, 70 mL/min×100 g of tissue, 80 mL/min×100 g of tissue, 90 mL/min×100 g of tissue, or 100 mL/min×100 g of tissue. Also in this aspect, attaining the maximum flow value 112 with the relevant potentiometer setting can be indicated by, for example, an LED indicator 94, which can light when the potentiometer 75 reaches the desired value. This determination step is represented by step 204 of FIG. 2.

Because the calibration described herein uses the heat balance Fourier equation shown in equation (1) below, which demonstrates a linear relationship between the heater power dissipation and a flow rate, only two data points are needed to provide the calibration. As explained above, these two data points are typically obtained near the minimum and maximum blood flow for an animal or human. However, in some situations such as certain genetic populations, disease states, nutritional deficiencies, and the like, the range of blood flow may vary considerably from the roughly 5-50 mL/min×100 g of tissue. In these situations, calibration can be conducted at smaller or different ranges as desired or needed, such as for example, 15-45 mL/min×100 g of tissue.

Calibration using a dry model device which references the wet model calibration. Routine use of a capillary blood flow wet model device is not practical or desirable, because it is inconvenient and even cumbersome. Therefore, this disclosure provides a dry model device which itself is calibrated using the wet model device. Specifically, the dry model device can employ thermal conductivity parameters obtained using the wet model device by translating them to thermal conductivity parameters in the dry model device which can be used to calibrate the capillary blood flow meter in absolute units. By calibrating the dry model to the wet model device data, rapid, routine, and convenient calibration of a capillary blood flow sensor 100 in absolute flow units can be achieved. Moreover, the dry model device can also be used in the scaled manufacturing of capillary blood flow systems 120.

Figure 4A:
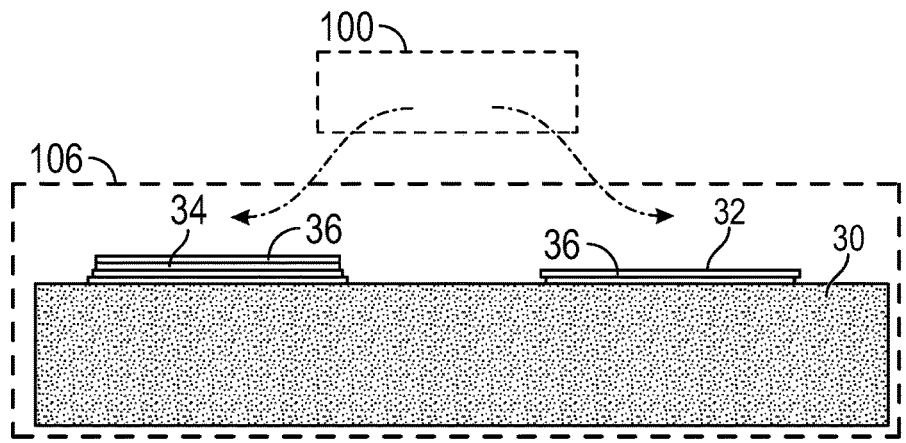
FIG. 4A illustrates an embodiment of the structure of a capillary blood flow dry model device including placement sites, specifically a first site and a second site, for the capillary blood flow sensor for calibration with the dry model device. In this embodiment, the first site and the second site are located on a single heat sink.
Figure 4B:
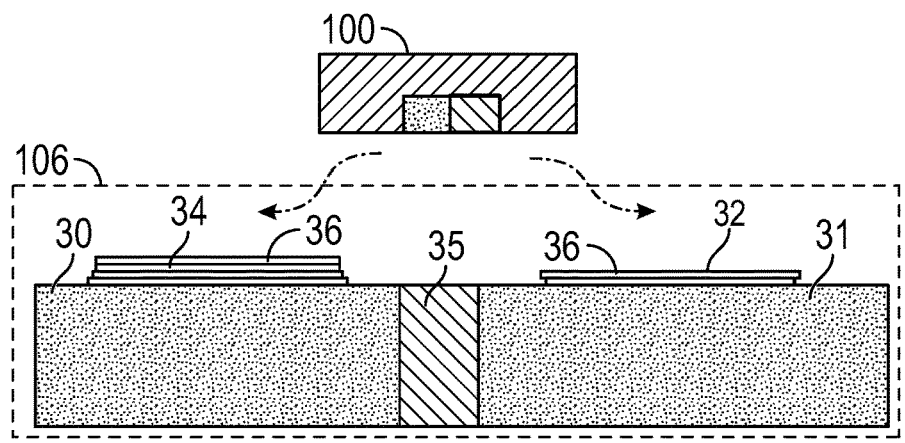
FIG. 4B illustrates an embodiment of the structure of a capillary blood flow dry model device including placement sites, specifically a first site and a second site, for the capillary blood flow sensor for calibration with the dry model device. In this embodiment, the first site is located on a first heat sink and the second site are located on a second heat sink, which are separated by a thermal insulator.

FIG. 4A illustrates an embodiment of the structure of a capillary blood flow dry model device including placement sites for the capillary blood flow sensor for calibration with the dry model device. The minimum and maximum of capillary blood flow values, which have been measured and set by means of the capillary blood flow wet model device 108 can be incorporated as heat conductivity parameters into the capillary blood flow dry model device 106, as illustrated as step 206 of FIG. 2.

The capillary blood flow dry model device 106 illustrated in FIG. 4A is represented by a flat metal plate of non-ferrous metal, for example copper or aluminum, having two separate measuring sites. Each measuring site includes one or more layers of a low heat conducting (or low heat conductive) material, for example, thin transparent polymer films or tapes, which can be adhesive polymer tapes. These layers can be applied layer-on-layer, and the number of layers applied to each site are used to provide an adjustment of the heat conductivity at that site. The capillary blood flow sensor 100, which is placed in thermal contact with one of the sites, can measure the heat conductivity value which corresponds to a certain number of layers of material, for example, polymer film layers.

While not intending to be bound by theory, a metal heat sink used in this method and apparatus has a very high heat conductivity. The low heat conductive polymer film or tape which is not considered heat conducting, is layered onto the heat sink at the placement site. Therefore, this method involves placing layers of a polymer film or tape material that has a low, finite heat conductivity over the surface of the heat sink that approaches an infinite heat conductivity. The layered placement sites can be considered to have a "residual conductivity" because they are thin and are layered on a surface of essentially an infinite conductivity.

FIG. 4B illustrates another aspect of the dry model device, in which the placement sites are located on thermally separated heat sinks. For example, in FIG. 4B, the first site is located on a first heat sink and the second site are located on a second heat sink, which are separated by a thermal insulator. For example, FIG. 4B illustrates a first heat sink 30 which is thermally isolated from the second heat sink 31 by an thermal insulator 35. Alternatively, element 35 can be absent such that the first heat sink 30 is not physically attached even indirectly with the second heat sink 31. In any embodiment, however, the operation of the dry model device in FIG. 4B is the same as the operation of the dry model device in FIG. 4A.

Determining a capillary blood flow in absolute flow units is obtained from the thermal conductivities of the dry model using the formula of the heat balance Fourier equation shown in equation (1), based on the capillary blood flow measurement being analogous to the measurement of heat conductivity of the material under the heater (or microheater) of the thermal capillary blood flow sensor:

$$Q/S = k\, dT/L, \tag{1}$$

wherein:
S=area under the heater;
Q=heater power;
k=thermal conductivity of the one or more layers of a low heat conductive material;
dT=temperature gradient;
L=thickness of the one or more layers of the material;
wherein the thermal conductivity (k) of equation (1) corresponds to absolute flow units according to equation (2), when dT is constant:

$$k = \text{flow} = V + PQ, \text{ and} \tag{2}$$

wherein V and P are parameters of characteristic linearity of the operation amplifier 88 in FIG. 6. By stating that k equals flow in flow units in equation (2), it is understood that k is equal to flow. In equation (1) and equation (2), the units of the variables and parameters can be any units that are internally consistent with each equation. A full treatment of heat transfer and Fourier's law can be found at, for example, Lienhard, John H. IV; Lienhard, John H. V (2008) *A Heat Transfer Textbook* (3rd ed.), Phlogiston Press, Cambridge, Mass. (ISBN 978-0-9713835-3-1), which is incorporated herein by reference in pertinent part.

In one aspect, the one or more layers of material used in the dry model can be any layer of material that has a low thermal conductivity, that is a low, finite heat conductivity, so that the thermal conductivity at each placement site can be adjusted by the thickness or number of layers of material. In an aspect, for example, the material can be plastic film, tape such as a tape (for example, SCOTCH® brand tape), a resin material that can be adjusted according to the thickness of the material applied to the site, plastic wrap material, and the like. In this disclosure, any description of adjusting the conductivity of a site by adding or removing layers is intended to encompass adjusting the thermal conductivity of a site by changing the thickness of a single layer.

By changing (adding or subtracting) the number of layers of material such as a film on both sites of the capillary blood flow dry model device 106, it is possible to attain those values of the capillary blood flow meter 102 which will correspond to the same values of a first fluid flow and a second fluid flow which were previously measured on the capillary blood flow wet model device. This aspect of the system and method is represented by step 208 and step 212 of FIG. 2.

Therefore, according to an aspect of the disclosure, there is provided a method for calibrating a capillary blood flow meter in absolute flow units, in which the method can comprise:

a) providing a capillary blood flow sensor comprising [1] a heater for changing the temperature of an area of a surface from a first temperature to a second temperature and for maintaining a constant temperature gradient between the first and second temperatures, and a power source for providing a power to the heater, and [2] a temperature sensor for measuring temperature at the area of the surface;

b) providing a wet model device comprising a flow path for a flowing fluid which is maintained at physiological temperature, one portion of which is covered by a barrier material having a top surface and a bottom surface and in contact with the flowing fluid on the bottom surface, and having a sufficient area for the heater and the temperature sensor to simultaneously contact the top surface of the barrier material;

c) [1] initiating a preselected first fluid flow along the flow path and determining a corresponding first heater power dissipation in order to maintain the temperature gradient constant and [2] initiating a preselected second fluid flow along the flow path and determining a corresponding second heater power dissipation in order to maintain the temperature gradient constant;

d) providing a dry model device comprising a first site on a first heat sink and a second site on a second heat sink and translating the first heater power dissipation and the second heater power dissipation of the wet model device to the thermal conductivity parameters at the first site and at the second site by [1] adjusting the thermal conductivity at the first site when the heater is operated at the first power determined using the wet model device, to maintain the temperature gradient constant, and [2] adjusting the thermal conductivity at the second site when the heater is operated at the second heater power determined using the wet model device, to maintain the temperature gradient constant; and e) calibrating a capillary blood flow sensor in absolute flow units using the dry model device by assigning the first heater power to correspond to the preselected first fluid flow and assigning the second heater power to correspond to the preselected second fluid flow.

In one aspect, the thermal conductivity at a first site and the thermal conductivity at a second site can be adjusted by applying or removing, independently, one or more layers of a material to the first site and the second site sufficient to maintain the constant predetermined temperature gradient at the preselected first fluid flow and preselected second fluid flow in the wet model device, respectively. Any adjustment to the thickness of the material at the first placement site and second placement site adjusts the thermal conductivity at that site, as explained above. A material can comprise or can be selected from, for example, a film such as a plastic tape.

In one aspect, the capillary blood flow sensor can comprise the heater and the temperature sensor integrated into a single unit, which is referred to herein as a capillary blood flow sensor module, which provides convenience in making measurements.

In one aspect, the fluid used in the wet model device can have physical properties that are similar to those of blood, for example, heat capacity, density and the like. In an aspect, the heat capacity of the fluid used in the wet model device can be within ±7%, ±5%, ±4%, ±3%, ±2%, or ±1% of the heat capacity of blood. For example, an aqueous solution of NaCl (sodium chloride) can be adjusted in concentration to achieve a solution having the heat capacity and density of blood which is particularly useful in the wet model device described herein.

Regarding the preselected first fluid flow and the preselected second fluid flow, because the calibration curve according to equations (1) and (2) above is linear, two data points are needed to generate the calibration, although additional data points can be used to provide a more accurate calibration. It can be useful to provide one of the preselected first fluid flow or the preselected second fluid flow is from about 1 mL/min×100 g of tissue to about 5 mL/min×100 g of tissue (milliliters per minute per 100 grams of tissue). It also can be useful to provide the other of the preselected second fluid flow or the preselected first fluid flow from about 60 mL/min×100 g of tissue to about 100 mL/min×100 g of tissue (milliliters per minute per 100 grams of tissue). In this aspect, the calibration uses flow values that correspond to the near minimum and near maximum of human capillary blood flow.

In a further aspect, the heater can comprise an electric heater, and in a particular aspect, the heater can comprise or be a silicon diode. The temperature sensor also can comprise or can be a silicon diode. In embodiments, the heater can comprise a first silicon diode, the temperature sensor can comprise a second silicon diode, and the first and second silicon diodes can be arranged in a diode array. In addition, the temperature sensor also can comprise or can be a silicon diode which can also operate to function as a heater or an electrical heating means.

In one aspect, the heat conductivity parameters corresponding to the capillary blood flow dry model device can be transferred and set by means of a calibrating unit 104 illustrated in FIG. 1 and FIG. 6, which interfaces directly with the capillary blood flow meter 102. This aspect is illustrated at step 210 and step 214 of FIG. 2. In this way, the correlation between fluid flow parameters of the capillary blood flow wet model device 108 and the thermal conductivity parameters of the capillary blood flow dry model device 106 by way of calibrating unit 104 are established. This method and the associated devices have enabled a relatively simple, compact and cost effective calibrating unit 104 to be easily interfaced with and integrated into the capillary blood flow meter 102 shown in FIG. 6. In turn, the method and the associated devices also allow for a wide range of convenient capillary blood flow measuring devices, which allow routine and simple measurement of capillary blood flow in absolute terms.

Regarding the calibration process that is carried out by the capillary blood flow meter, in an aspect, this disclosure provides a process for calibrating a capillary blood flow sensor (or calibrating a blood flow meter) in absolute flow units, in which the process can comprise:

a) contacting a capillary blood flow sensor with a first site on a first heat sink of a dry model device, wherein the capillary blood flow sensor comprises a heater and a temperature sensor;

b) activating a control signal (b) to measure a first temperature of the first site, then deactivating the control signal (b);

c) activating a control signal (a) to turn ON the heater for a predetermined time period to heat the sensor on the first site to a second temperature, wherein the temperature gradient between the first temperature and the second temperature is maintained constant at +x° C.;

d) activating a control signal (c) to measure the heater power required to maintain the temperature gradient constant;

e) activating a control signal (d) to turn ON a calibrating unit and converting the heater power dissipation to a measured flow rate based upon the dry model device;

f) comparing the measured flow rate based upon the dry model device to a first absolute flow rate based upon a wet model device;

g) adjusting the number of layers or the thickness of a material on the first site of the dry model device to reduce the difference between the measured flow rate and the first absolute flow rate;

h) repeating steps f) and g) as needed until the difference between the measured flow rate based upon the dry model device and the first absolute flow rate based upon the wet model device is 0; and i) repeating steps a) through h) by contacting the capillary blood flow sensor with a second site on a second heat sink of the dry model device. In this repeating step, the measured flow rate based upon the dry model device are compared to a second absolute flow rate based upon the wet model device and the number of layers or the thickness of a material on the second site of the second heat sink of the dry model device are adjusted until the difference between the measured flow rate based upon the dry model device and the second absolute flow rate based upon the wet model device is 0.

Moreover, this process can further comprise the step of: e) 1) displaying the measured flow rate based upon the dry model device on a display device. A display device is illustrated in FIG. 1, which provides a very convenient means of carrying out the calibration by providing quickly readable values that can be further adjusted.

In one aspect, the process for calibrating a capillary blood flow sensor (or calibrating a blood flow meter) in absolute flow units can further comprise the steps of:

j) deactivating control signal (d) to turn OFF the calibrating unit;

k) deactivating control signal (c) to terminate measurement of the heater power dissipation; and l) deactivating control signal (a) to turn OFF the heater.

In addition, this disclosure provides a computer, in which the computer can comprise a processor; and a non-transitory computer recordable storage medium in communication with the processor, the non-transitory computer recordable storage medium storing program code, which when executed by the processor, performs a computer-implemented process for calibrating a capillary blood flow sensor in absolute flow units as described immediately above.

Figure 3:
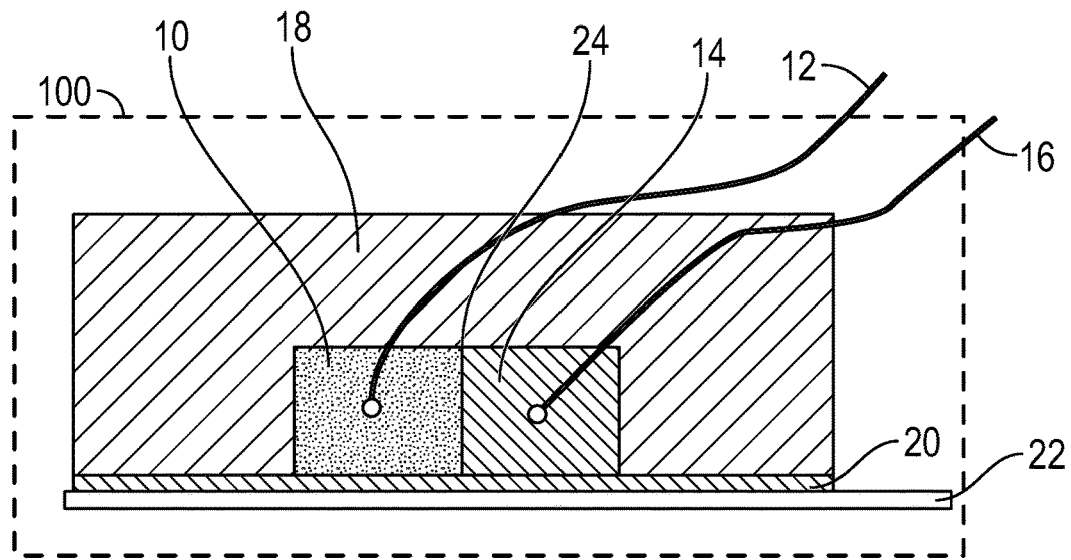
FIG. 3 provides a cross sectional illustration of the structure of the capillary blood flow sensor according to a U.S. Pat. No. 6,221,025, which can be used according to the present disclosure. Shown in FIG. 3 is the capillary blood flow sensor module embodiment, in which the heater and the temperature sensor are combined into a thermally insulated capillary blood flow sensor module. As illustrated in the embodiment of FIG. 3, the capillary blood flow sensor module is thermally insulated around the sides and on top, that is, it is thermally insulated on the portions of the sensor module unit that are not in contact with the skin or the surface to be heated and measured.

Structure of the capillary blood flow sensor and the dry model device. FIG. 3 provides a cross sectional illustration of the structure of the capillary blood flow sensor 100 (see also FIG. 1) according to a U.S. Pat. No. 6,221,025, which can be used according to the present disclosure. Referring to FIG. 3, capillary blood flow sensor 100 is based on a temperature sensor 10 with output connections 12 and a micro-heater (or simply, a heater) 14 with input connections 16. The temperature sensor 10 and micro-heater 14 are connected by a heat-conducting material 24, such that they are in thermal contact. This assembly of temperature sensor 10, micro-heater 14, and heat-conducting material 24 which connects 10 and 14 may be referred to herein as a "micro-chip". In one aspect, the micro-chip can include two electrically isolated semi-conductive elements, for example, silicon diodes, in which one of the silicon diodes can be used as a temperature sensor, and the other silicon diode can be used as a micro-heater.

In an aspect, the heat conducting material 24 can comprise or can be selected from a heat conducting epoxy material. This material fixes the temperature sensor 10 to the micro-heater 14 to provide the micro-chip assembly, and it provides reliable thermal contact between the temperature sensor 10 and micro-heater 14. As illustrated in FIG. 3, the lower surface of the micro-chip is the working or sensing portion of the micro-chip. In embodiments, the top and lateral (side) surfaces of temperature sensor 10 and micro-heater 14 combination, essentially the micro-chip assembly, can be covered with a thermal insulator 18, for example, a porous adhesive material. The lower (working or sensing) surface together with the bottom surface of the thermal insulator 18 can be covered by an adhesive layer 20, for example, a double-sided thin medical adhesive. To maintain and protect the adhesive layer 20 prior to the installation of capillary blood flow sensor 100 on a measuring site, a protective cover 22 can be used if desired. For example, protective cover 22 can be a thin plastic type material which is removed to expose the sensor surface prior to measurement.

FIG. 4A illustrates an embodiment of the structure of a capillary blood flow dry model in which a first placement site and a second placement site for the capillary blood flow sensor or sensor module are located on a single heat sink, whereas FIG. 4B illustrates an embodiment of the structure of a capillary blood flow dry model device the first site is located on a first heat sink and the second site are located on a second heat sink, which are separated by a thermal insulator In FIG. 4B, the first heat sink 30 is thermally isolated from the second heat sink 31 by an thermal insulator 35. The operation of the dry model device of FIG. 4A is identical to the operation of the dry model device of FIG. 4B. Therefore, the following discussion of the operation of the dry model device in FIG. 4A is likewise applicable to the operation of the FIG. 4B dry model device.

FIG. 4A and FIG. 4B illustrate embodiments of the structure of a capillary blood flow dry model device 106 including placement sites for the capillary blood flow sensor for calibration with the dry model device. Dry model device 106 can include a flat metal plate 30, for example a copper or aluminum metal plate, which can enable efficient heat transfer and provide a stable temperature. The upper surface of the metal plate can be polished to provide good thermal contact at the surface.

In embodiments, two separate measuring sites can be situated on the upper polished surface of the metal plate 30 as shown in FIG. 4A. In FIG. 4B, two separate measuring sites can be situated on the upper polished surfaces of two different metal places, a first metal plate 30 and a second metal place 31. Each measuring site includes one or more layers of material, for example, thin transparent polymer films or tapes, shown in FIG. 4A and FIG. 4B as plastic layer 34 and plastic layer 32, having a specific distance between them so that each is thermally isolated from the other. Plastic layer 34 and plastic layer 32 can have an area or a circumference that slightly exceeds the area or the circumference of the capillary blood flow sensor 100, so that the capillary blood flow sensor fits over the area. Even though the term "plastic layer" is used to refer to 34 and 32 at the separate measuring sites, these sites can include multiple layers of material (an individual layer is shown as 36 in FIG. 4A and FIG. 4B) which can be applied layer-on-layer, and the number of layers applied to each site are used to provide an adjustment of the heat conductivity at that site. The capillary blood flow sensor 100, which is placed in thermal contact with one of the sites, can measure the heat conductivity value which corresponds to a certain number of layers, for example, adhesive film layers.

The dry model device can be standardized to reflect the wet model device absolute flow rate information by translating the minimum thermal conductivity and the maximum thermal conductivity from the wet model device. This allows translation of the thermal conductivity parameters at the first heat sink and at the second heat sink (34 and 32 of FIG. 4A) by adjusting the thickness or the number or quantity of thin polymer tape layers at each site, as follows. The quantity of thin tape layers can be established such that the common heat conductivity of plastic layer 34 corresponds to the minimum value (5 mL/min×100 g of tissue) of the heat conductivity scale of the capillary blood flow meter. The plastic layer 32 is made similarly, but the number of individual thin tape layers 36 of the same type is established so that the common heat conductivity of the plastic layer 32 corresponds to the maximal value (50 mL/min×100 g of tissue) of the heat conductivity scale of the capillary blood flow meter.

Placing, affixing, or simply situating the sensor on plastic layer 34 and plastic layer 32 for measurement of their heat conductivity is illustrated in FIG. 4A by the dotted arrows, in which the metal plate 30 functions as a heat sink which provides stable temperature.

In an aspect, the capillary blood flow sensor or sensor module can be a disposable capillary blood flow sensor or sensor module. Alternatively, the capillary blood flow sensor or sensor module can be reusable.

Structure of the wet model device. FIG. 5 illustrates an embodiment of the capillary blood flow wet model device 108 according to this disclosure, which contrasts with previous wet model devices such as described in U.S. Pat. No. 5,205,293 and in Toumi, et al. The wet model device of the present disclosure is designed in a manner that more closely reflects the actual capillary blood flow, because it enables fluid flow which imitates actual capillary blood flow, which allows flow measurement in absolute flow rates to be made by the capillary blood flow sensor 100. The illustration of the wet model device of FIG. 5 including a cross sectional view of the upright internal fluid feeding tube and external receiving tube, which allow determination of the thermal conductivity corresponding to a preselected fluid flow along the flow path illustrated.

Referring to FIG. 5, in an aspect, the capillary blood flow wet model device 108 comprises an upright feed tube 42, the diameter of which slightly exceeds the diameter of the capillary blood flow sensor 100. The upright feed tube 42 can be made of any material which is structurally sufficient to manage the fluid flow, for example, plastic. Feed tube 42 can has perforated edges 44, which enable liquid to freely flow through them from the internal feeding tube 42 and be collected in an external receiving tube 40. Tubes 40 and 42 can be situated concentrically at their top ends. As shown in FIG. 5, the top ends can be closed by a barrier material 46, such as a thin plastic film, which ensures that the liquid will be contained within the system and will not flow out of the closed system.

Other elements of the wet model device 108 include heater 52 (not to be confused with the heater in the sensor or sensor module), thermo-sensor 54, thermostat 56, and syringe pump 58. Inside and at the upper end of feed tube 42 are situated heater 52 and a thermo-sensor 54, which are attached to and in communication with thermostat 56. The heater 52, thermo-sensor 54, and thermostat 56 provide the flowing liquid contained in the wet model device 108 with a stable and adjustable temperature in the vicinity of the capillary blood flow sensor 100. For calibrating capillary blood flow measurements, the liquid temperature is maintained at about 36° C. The liquid flow at entrance 48 is provided by syringe pump 58, which imparts a stable and controlled speed to the liquid flow, which approximates the actual speed (absolute flow rate) of capillary blood flow. This system can be provided with a designated port 50 in order for the liquid to exit the system and if desired, to be recycled by syringe pump 58 through the entrance 48.

During operation of the wet model device, liquid is constantly flowing due to the pump action, and liquid flows into feed tube 42 and reaches the perforated edges 44, which can be holes. Liquid exits the feed tube 42 through the holes or perforations and is collected in the external receiving tube 40 and can be recycled again. The bottom surface of barrier material 46 is always in contact with the flowing liquid as it flows and exists the perforations or holes. Any structure which allows the flowing liquid to be in contact with the bottom surface of the barrier material while allowing the liquid to also flow through any type of holes or perforations can be used.

Figure 7:
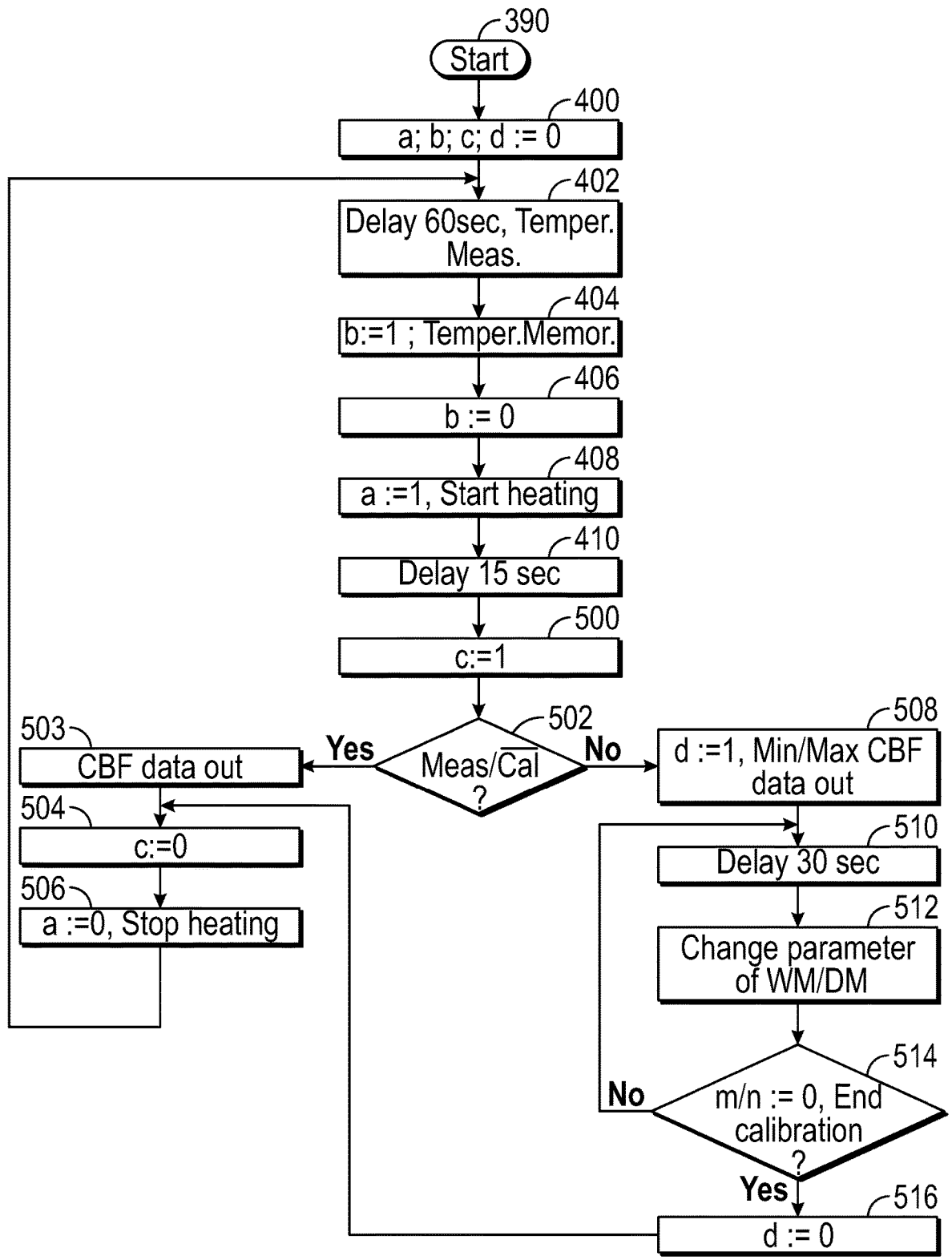
FIG. 7 illustrates a sequence for the functioning of the main components, units, and devices presented in FIG. 6, and in particular illustrates an operational algorithm for the capillary blood flow meter and associated units represented in FIG. 6.

Operation of the capillary blood flow meter and calibrating unit. In an aspect, the structure of the capillary blood flow meter 102 together with the calibrating unit 104 is presented in FIG. 6, and the method of its operation is presented on FIG. 7 in flowchart form. Specifically, FIG. 6 illustrates a schematic block diagram of the structure of the capillary blood flow meter according to U.S. Pat. No. 6,221,025, which further includes an additional calibrating unit according to the present disclosure, which is constructed and operative in accordance with the present disclosure, with both temperature sensing apparatus and heating apparatus being constituted by silicon diodes. FIG. 7 illustrates a sequence for the functioning of the main components, units, and devices presented on FIG. 6, and in particular illustrates an operational sequence for capillary blood flow meter and units represented in FIG. 6. The capillary blood flow meter 102 of this disclosure adds new capabilities to the capillary blood flow meter disclosed in U.S. Pat. No. 6,221,025, including rapid and routine calibration methods and devices for absolute blood flow.

Referring to FIG. 6, to achieve accurate temperature and heat flow measurements using the capillary blood flow sensor 100, that is, measurements under the sensor, a digital memory, an analog-to-digital converter 66 and a digital-to-analog converter 68 can be employed. These converters are sequentially connected one to the other and transfer a digital code, the length of which provides accuracy of not less than 0.5%.

Regulator 62 of FIG. 6 supplies a stable reference voltage which is transferred to an instrumental amplifier 72. Potentiometer 84, which corresponds to the parameter V in the formula of equation (2), can shift the level of the output voltage in the operational amplifier 88. Variable resistor 86 can establish a characteristic of the signal relayed to the operational amplifier 88, in which the linear slope corresponds to parameter P of amplification in equation (2).

A signal corresponding to a flow measurement initiates as the voltage proceeds from the output of the instrumental amplifier 72 to the input of the voltage follower 71, and then through variable resistor 70 to switch 64. In the ON mode of switch 64, the current is supplied to micro-heater 14 of the capillary blood flow sensor 100. The same voltage signal corresponding to the flow measurement also proceeds to the input of the operational amplifier 88.

The instrumental amplifier 72 receives a voltage signal into its inverting input from digital-to-analog converter 68. On the same instrumental amplifier 72, the non-inverting input receives the voltage signal from a temperature sensor 10 of the capillary blood flow sensor 100. The voltage signal of the temperature sensor 10 provides current through resistor 60, and the same voltage proceeds to the input of the analog-to-digital converter 66.

The calibrating unit 104 contains two comparators 92 and 90, reflecting the minimum and maximum of the flow signal, respectively, which can be indicated using LED indicators 96 and 94 if desired. Adjustments of the minimum and the maximum of both comparators can be made by potentiometers 76 and 75, respectively. A stable voltage from regulator 62 is supplied to potentiometers 76 and 75. Outputs from potentiometers 76 and 75 are connected to contralateral inputs of the comparators 92 and 90. The second contralateral inputs of comparators 92 and 90 are connected together and connected to the output of the operational amplifier 88, FIG. 6.

Accordingly, in an aspect, this disclosure provides a method for measuring capillary blood flow in absolute flow units, the method a) providing a capillary blood flow sensor comprising [1] a heater for applying heat to an area of skin to change the temperature of the skin from a first temperature to a second temperature and for maintaining a constant temperature gradient between the first and second temperatures, and a power source for providing a power to the heater, and [2] a temperature sensor for measuring temperature at the area of skin;

b) with the temperature sensor, measuring the first temperature at the area of skin;

c) with the heater, applying heat to the area of skin to change the first temperature to a second temperature and maintaining the temperature gradient constant;

d) measuring the heater power dissipation required to maintain the temperature gradient constant; and e) determining a capillary blood flow in absolute flow units by comparing the heater power dissipation with a linear relationship based upon the Fourier equation of flow;

wherein the capillary blood flow sensor is calibrated by:

f) providing a wet model device comprising a flow path for a flowing fluid which is maintained at physiological temperature, one portion of which is covered by a barrier material having a top surface and a bottom surface and in contact with the flowing fluid on the bottom surface, and having a sufficient area for the heater and the temperature sensor to simultaneously contact the top surface of the barrier material;

g) [1] initiating a preselected first fluid flow along the flow path and determining a corresponding first heater power in order to maintain the temperature gradient constant and [2] initiating a preselected second fluid flow along the flow path and determining a corresponding second heater power in order to maintain the temperature gradient constant;

h) providing the dry model device comprising a first site on a first heat sink and a second site on a second heat sink and translating the first heater power and the second heater power of the wet model device to the thermal conductivity parameters at the first site and at the second site by [1] adjusting the thermal conductivity at the first site when the heater is operated at the first heater power to maintain the temperature gradient constant, and [2] adjusting the thermal conductivity at the second site when the heater is operated at the second heater power to maintain the temperature gradient constant; and i) calibrating a capillary blood flow sensor in absolute flow units using the dry model device by assigning the first heater power to correspond to the preselected first fluid flow and assigning the second heater power to correspond to the preselected second fluid flow.

In establishing the constant temperature gradient, it is not necessary to measure the second temperature, because the constant thermal gradient can be established based upon knowledge of the first temperature. The heater power, Q, changes according to changes in capillary blood flow. However, an added feature of the method and apparatus described herein is that the skin temperature is obtained during their operation and can be displayed, which can provide additional diagnostic information. In an aspect, the method and apparatus can provide the skin temperature having an accuracy of about ±0.3° C., about ±0.2° C., or about ±0.1° C.

Thus, the thermal conductivity at the first site (first placement site) and the thermal conductivity at the second site (second placement site) can be adjusted by applying or removing, independently, one or more layers of material to the first site and to the second site sufficient to maintain the constant predetermined temperature gradient at the preselected first fluid flow and the preselected second fluid flow in the wet model device, respectively. In embodiments, the first heat sink and the second heat sink can be combined into one continuous heat sink, comprising the first site and the second site.

As explained previously, determining a capillary blood flow in absolute flow units is obtained from the thermal conductivities of the dry model using the equation (1), wherein the thermal conductivity (k) of equation (1) corresponds to flow units according to equation (2), as set out in this disclosure.

In embodiments, measuring the first temperature and applying a constant predetermined temperature gradient can be conducted with a capillary blood flow sensor module comprising a heater and the temperature sensor integrated into a single unit, which can be thermally insulated on the portions of the sensor module unit that are not in contact with the skin or the surface to be heated and measured. In aspects, the heater can comprise a first silicon diode, the temperature sensor can comprise a second silicon diode, and the first and second silicon diodes can be arranged in a diode array, in which the first diode and the second diode are electrically insulated from each other.

This disclosure also provides a process for measuring a capillary blood flow on a subject in absolute flow units, in which the process can comprise:

a) contacting a capillary blood flow sensor with an area of skin of a subject, wherein the capillary blood flow sensor comprises a heater and a temperature sensor;

b) activating a control signal (b) to measure a first temperature of the skin, then deactivating the control signal (b);

c) activating a control signal (a) to turn ON the heater for a predetermined time period to heat the area of the skin to a second temperature, wherein the temperature gradient between the first temperature and the second temperature is maintained constant at +x° C.;

d) activating a control signal (c) to measure the heater power required to maintain the temperature gradient constant; and e) converting the heater power dissipation to the capillary blood flow in absolute flow units.

This process can further comprise the step of: f) displaying the capillary blood flow in absolute flow units on a display device. A display device is illustrated in FIG. 1, which provides a very convenient means of carrying out the calibration by providing quickly readable values that can be further adjusted.

In an aspect, this process can further comprise the steps of:

g) deactivating control signal (c) to terminate measurement of the heater power dissipation; and h) deactivating control signal (a) to turn OFF the heater. Further, the process set out above can further comprise repeating steps a) through h) to obtain additional measurements of capillary blood flow in absolute flow units.

As explained, converting the heater power dissipation to the capillary blood flow in absolute flow units is performed according to equations (1) and (2) presented herein.

Also regarding this process for measuring a capillary blood flow in absolute flow units, as disclosed in this process, the heater can be turned ON for a predetermined time period. In an aspect of this process, this process can be about 5 seconds, about 10 seconds, about 15 seconds, about 20 seconds, or about 25 seconds, or can be other predetermined time periods.

In addition, this disclosure provides a computer, in which the computer can comprise a processor; and a non-transitory computer recordable storage medium in communication with the processor, the non-transitory computer recordable storage medium storing program code, which when executed by the processor, performs a computer-implemented process for measuring a capillary blood flow on a subject in absolute flow units as described above.

In one aspect of this process, the temperature gradient of +x° C. can be maintained with a negative feedback loop through an instrumental amplifier 72 and a voltage follower 71 in FIG. 6. As in the capillary blood flow device and sensor described by this inventor in U.S. Pat. No. 6,221,025, the instrumental amplifier, follower and resistor with the negative thermal feedback through the first and second diodes are employed to maintain a stable and constant temperature gradient. Further, the temperature gradient of +x° C. can be selected with a variable resistor 70. Exemplary temperature gradients+x° C. can be, for example, +0.5° C., +1.0° C., +1.5° C., +2.0° C., +2.5° C., +3.0° C., +3.5° C., +4.0° C., +4.5° C., or +5.0° C. In one aspect, the temperature gradients+x° C. can be from about +1.5° C. to about +2.5° C. It has been found that if the temperature gradient is maintained at about +2.0° C., a human subject generally cannot discern any heating when the capillary blood flow sensor module contacts the skin and measurements are made, and most subjects report that any sensation of heating is imperceptible.

Referring now to FIG. 6 and FIG. 7, the structure, control and operation of the capillary blood flow sensor 102 with the calibration unit 104 shown schematically in FIG. 6 are illustrated, in which the capillary blood flow sensor (or sensor module) can be operated according to the scheme or algorithm shown on FIG. 7. Specifically, the capillary blood flow sensor with the calibration unit of FIG. 6 can function in two main operational modes: [1] a measurement mode, MEAS; and [2] a calibration mode, also referred to as a calibration-measurement mode, CALIB. The measurement mode, MEAS, can be used in a variety of different situations, for example [1] to establish the characteristic linear parameters V and P of the capillary blood flow meter 102 and to establish the relevant values of potentiometers 75 and 76 (FIG. 6) of calibration unit 104, by means of the capillary blood flow wet model 108, and [2] for routine measurements on subjects, after the capillary blood flow meter 102 is adjusted and the capillary blood flow sensor 100 has already been calibrated.

Control unit 82 (FIG. 6) provides, according to the operational sequence in FIG. 7, a sequence of control signals for a portion of the above described units based on the signals at 502 labelled MEAS/CALIB and at 390 labelled START. Specifically, in the MEAS mode, after the START command facilitated by the control unit 82 (FIG. 6) and in accordance to step 400 (FIG. 7), the control signals a, b, c and d are set to zero. Switch 64 and switch 98 are disconnected, therefore transmission of the digital code of the first temperature to the digital-to-analog converter 68 is disabled and the calibrating unit 104 is turned OFF. Step 402 has a delay period, for example, a delay of 60 seconds, which is used for establishing a steady-state temperature balance, that is, for equilibrating the temperature, of the capillary blood flow sensor 100 (FIG. 6). In step 404 (FIG. 7) a control signal b (FIG. 6) is activated in which a voltage signal corresponding to the first temperature of a temperature sensor 10 through the analog-to-digital converter 66 is transferred to the digital-to-analog converter 68, and can be placed in the memory in the form of a multi-bit digital code.

Step 406 (FIG. 7) turns OFF the control signal b, which disables delivery of a next digital code to the digital-to-analog converter 68. At the same time, the first temperature signal from temperature sensor 10 which was placed in the memory when the micro-heater 14 was switched OFF, proceeds to the inverting input of the instrumental amplifier 72.

Then, step 408 activates the control signal a, turning ON switch 64, in such that the voltage signal from voltage follower 71 transforms to current by means of the variable resistor 70 and activates the micro-heater 14. With step 410, heating continues for a predetermined time period, for example, 15 seconds, in order to establish a new steady-state temperature balance or equilibrium of the system containing the temperature sensor 10 and the micro-heater 14. At this new steady-state temperature balance, the temperature gradient is +x° C., which can be for example, +2.0° C. The stability of this temperature gradient is achieved with, for example, a negative feedback loop through the instrumental amplifier 72 and the voltage follower 71. The variable resistor 70 can, within a small range, be used to change the temperature gradient to a desirable value other than +2.0° C.

Step 500 of FIG. 7 activates the control signal c which turns ON switch 98 of FIG. 6 and after steps 502 and 503, the measured capillary blood flow signal is transferred to the display 110.

Subsequently, step 504 through control signal c turns OFF switch 98 and as such shuts down the capillary blood flow output signal. Step 506 turns OFF the control signal a, and so turns OFF switch 64 which interrupts heating of micro-heater 14. A new measurement is initiated with step 402 (FIG. 7). In this manner, each cycle of measurement of capillary blood flow takes about 1.5 minutes.

The calibration-measurement mode, CALIB, is used for adjustment of parameters of the capillary blood flow dry model device 106 after the capillary blood flow wet model device 108 has been used to establish the appropriate range of flow values. In the CALIB mode, the capillary blood flow sensor 100 (FIG. 6) is installed on site 32 or 34 of the capillary blood flow dry model device 106 (FIG. 4A). After the START and execution of steps from 400 to 500 of FIG. 7, a transition through step 502 to step 508 enables the control signal d to activate and turn ON the calibrating unit 104 (FIG. 6). Depending upon which of the two sites (first site 32 or second site 34) of the capillary blood flow dry model 106 that the capillary blood flow sensor 100 was placed on, the corresponding value of the flow signal is measured. This flow signal information can be transmitted to a display 110. Step 510 initiates a time delay, for example a delay of 30 seconds. which allows the operator to compare the received flow value to the corresponding first (minimum) or second (maximum) value of flow received earlier on the capillary blood flow wet model device 108 (FIG. 6). Step 512 shows the changes to the thermo-conductivity parameter of the dry model device 106 (FIG. 4A) in accordance with comparison. For example, the number of layers of a material on each heat sink (or each site of a heat sink) of the dry model device to reduce the difference between the measured flow rate and the absolute flow rate obtained in the wet model device.

Step 510 and 512 of FIG. 7 can be repeated cyclically until the condition in step 514 is fulfilled such that the (subsequent) control signals m and n from the output of the calibrating unit 104 will activate. This means that the parameters of minimum and maximum value of the flow signal will be equal to the corresponding values of liquid flow value on the capillary blood flow wet model device 108 (FIG. 6). Post-calibration, there is a transition to step 516, which simply turns OFF the calibrating unit 104. After switching OFF the calibration-measurement mode, the system can then work in the measurement mode through commands 504 and 506 as explained above.

After completion of the calibration-measurement mode (or simply, calibration mode), it is only necessary to use the operative capillary blood flow dry model device 106 (FIG. 4A) to quickly and efficiently calibrate the capillary blood flow sensor in absolute flow terms, rather than referring to the capillary blood flow wet model device 108 (FIG. 5). This need to use only the dry model device 106 provides certain other advantages, such as the ability to calibrate disposable capillary blood flow sensors 100, for the adjustment of new capillary blood flow systems 120 (FIG. 1) during manufacturing, and the like.

It will be understood that the methods and processes of the disclosure can be carried out with a device that has been described herein, and this disclosure provides a device for measuring capillary blood flow in absolute flow units, wherein the device can comprise:

a) a heater for applying heat to an area of skin to change the temperature of the skin from a first temperature to a second temperature and for maintaining a constant temperature gradient between the first and second temperatures, and a power source for providing power to the heater;

b) a temperature sensor for measuring temperature at the area of skin;

c) a controller in communication with the heater and the temperature sensor which [1] operates the heater for maintaining the temperature gradient constant and [2] operates the temperature sensor in a first operative mode and a second operative mode, wherein in the first operative mode the temperature sensor measures the first temperature at the area of skin, and wherein in the second operative mode, the controller operates the heater to maintain the temperature gradient constant between the first and second temperatures;

d) a processor in communication with the controller for determining a capillary blood flow in absolute flow units corresponding to the measured first temperature and the heater power dissipation required to maintain the temperature gradient constant; and e) a calibrating unit in communication with the processor which has been standardized in absolute flow units by: [1] in a wet model device, determining a first heater power dissipation corresponding to a preselected first fluid flow and determining a second heater power dissipation corresponding to a preselected second fluid flow, each in order to maintain the temperature gradient constant; [2] in a dry model device, adjusting the thermal conductivity of one or more layers at a first site on a first heat sink when the heater is operated at the first power obtained using the wet model device to obtain the constant temperature gradient at the preselected first fluid flow, and adjusting the thermal conductivity of one or more layers at a second site on a second heat sink when the heater is operated at the second power obtained using the wet model device to correspond to the constant temperature gradient at the preselected second fluid flow; and [3] standardizing the calibrating unit in absolute flow units using the dry model device by assigning the first heater power to correspond to the preselected first fluid flow and assigning the second heater power to correspond to the preselected second fluid flow.

Aspects of this disclosure are further set out in the following claims. Embodiments or aspects of this disclosure which are described as "comprising" certain steps or elements, alternatively, can "consist essentially of" or "consist of" those steps or elements, unless specifically stated otherwise.

What is claimed is:

1. A method for calibrating a capillary blood flow sensor in absolute flow units, the method comprising:

providing a capillary blood flow sensor comprising a heater for changing the temperature of an area of a surface from a first temperature to a second temperature and for maintaining a constant temperature gradient between the first and second temperatures, a power source for providing a power to the heater, and a temperature sensor for measuring temperature at the area of the surface;

providing a wet model device comprising a flow path for a flowing fluid which is maintained at physiological temperature, one portion of which is covered by a barrier material having a top surface and a bottom surface and in contact with the flowing fluid on the bottom surface, and having a sufficient area for the heater and the temperature sensor to simultaneously contact the top surface of the barrier material;

initiating a preselected first fluid flow along the flow path and determining a corresponding first heater power dissipation in order to maintain the temperature gradient constant, and initiating a preselected second fluid flow along the flow path and determining a corresponding second heater power dissipation in order to maintain the temperature gradient constant;

providing a dry model device comprising a first site on a first heat sink and a second site on a second heat sink and translating the first heater power dissipation and the second heater power dissipation of the wet model device to the thermal conductivity parameters at the first site and at the second site by adjusting the thermal conductivity at the first site when the heater is operated at a first heater power determined using the wet model device, to maintain the temperature gradient constant, and adjusting the thermal conductivity at the second site when the heater is operated at a second heater power determined using the wet model device, to maintain the temperature gradient constant in an adjusted dry model device; and calibrating a capillary blood flow sensor in absolute flow units using the adjusted dry model device by assigning the first heater power to correspond to the preselected first fluid flow and assigning the second heater power to correspond to the preselected second fluid flow.

2. The method according to claim 1, wherein the thermal conductivity at the first site and the thermal conductivity at the second site are adjusted by applying or removing, independently, one or more layers of a material to the first site and/or to the second site sufficient to maintain the temperature gradient constant at the preselected first fluid flow and preselected second fluid flow in the wet model, respectively.

3. The method according to claim 1, wherein the first heat sink and the second heat sink are combined into one continuous heat sink, comprising the first site and the second site.

4. The method according to claim 1, wherein the heater and the temperature sensor are combined into a capillary blood flow sensor module.

5. The method according to claim 1, wherein the heat capacity of the fluid is within ±5% of the heat capacity of blood.

6. The method according to claim 1, wherein one of the preselected first fluid flow or the preselected second fluid flow is from about 1 mL/min×100 g of tissue to about 5 mL/min×100 g of tissue (milliliters per minute per 100 grams of tissue).

7. The method according to claim 1, wherein one of the preselected second fluid flow or the preselected first fluid flow is from about 60 mL/min×100 g of tissue to about 100 mL/min×100 g of tissue (milliliters per minute per 100 grams of tissue).

8. The method according to claim 1, wherein the heater comprises a silicon diode.

9. The method according to claim 1, wherein the temperature sensor comprises a silicon diode.

10. The method according to claim 1, wherein the heater comprises a first silicon diode, the temperature sensor comprises a second silicon diode, and the first and second silicon diodes are arranged in a diode array and are electrically insulated from each other.

11. A method for measuring capillary blood flow in absolute flow units, the method comprising:

providing a capillary blood flow sensor comprising a heater for applying heat to an area of skin to change the temperature of the skin from a first temperature to a second temperature and for maintaining a constant temperature gradient between the first and second temperatures, a power source for providing a power to the heater, and a temperature sensor for measuring the first temperature at the area of skin;

with the temperature sensor, measuring the first temperature at the area of skin;

with the heater, applying heat to the area of skin to change the first temperature to a second temperature and maintaining the temperature gradient constant;

measuring the heater power dissipation required to maintain the temperature gradient constant; and determining a capillary blood flow in absolute flow units by comparing the heater power dissipation with a linear relationship based upon the Fourier equation of flow;

wherein the capillary blood flow sensor is calibrated by:
providing a wet model device comprising a flow path for a flowing fluid which is maintained at physiological temperature, one portion of which is covered by a barrier material having a top surface and a bottom surface and in contact with the flowing fluid on the bottom surface, and having a sufficient area for the heater and the temperature sensor to simultaneously contact the top surface of the barrier material;

initiating a preselected first fluid flow along the flow path and determining a corresponding first heater power dissipation in order to maintain the temperature gradient constant, and initiating a preselected second fluid flow along the flow path and determining a corresponding second heater power dissipation in order to maintain the temperature gradient constant;

providing the dry model device comprising a first site on a first heat sink and a second site on a second heat sink and translating the first heater power dissipation and the second heater power dissipation of the wet model device to the thermal conductivity parameters at the first site and at the second site by adjusting the thermal conductivity at the first site when the heater is operated at a first heater power determined using the wet model device, to maintain the temperature gradient constant, and adjusting the thermal conductivity at the second site when the heater is operated at a second heater power determined using the wet model device, to maintain the temperature gradient constant in an adjusted dry model device; and calibrating a capillary blood flow sensor in absolute flow units using the adjusted dry model device by assigning the first heater power to correspond to the preselected first fluid flow and assigning the second heater power to correspond to the preselected second fluid flow.

12. The method according to claim 11, wherein the thermal conductivity at the first site and the thermal conductivity at the second site are adjusted by applying or removing, independently, one or more layers of a material to the first site and/or to the second site sufficient to maintain the temperature gradient constant at the preselected first fluid flow and preselected second fluid flow in the wet model, respectively.

13. The method according to claim 11, wherein determining a capillary blood flow in absolute flow units is obtained from the thermal conductivities of the dry model or the adjusted dry model using the equation (1):

$$Q/S=kdT/L \quad (1),$$

wherein:
S=area under the heater;
Q=heater power;
k=thermal conductivity of the one or more layers of a low heat conductive material;
dT=temperature gradient;
L=thickness of the one or more layers of material;
wherein the thermal conductivity (k) of equation (1) corresponds to absolute flow units according to equation (2):

$$k=\text{flow}=V+PQ/dT \quad (2), \text{ and}$$

wherein V and P are parameters of characteristic linearity of an operation amplifier, and wherein when dT is constant, k=flow=V+P Q.

14. The method according to claim 11, wherein measuring the first temperature and maintaining a temperature gradient constant are conducted with a capillary blood flow sensor module comprising a heater and the temperature sensor integrated into a single unit.

15. The method according to claim 11, wherein the heater comprises a silicon diode.

16. The method according to claim 11, wherein the temperature sensor comprises a silicon diode.

17. The method according to claim 11, wherein the heater comprises a first silicon diode, the temperature sensor comprises a second silicon diode, and the first and second silicon diodes are arranged in a diode array and are electrically insulated from each other.

18. The method according to claim 11, wherein the heat capacity of the fluid is within ±5% of the heat capacity of blood.

19. The method according to claim 11, wherein one of the preselected first fluid flow or the preselected second fluid flow is from about 1 mL/min×100 g of tissue to about 5 mL/min×100 g of tissue (milliliters per minute per 100 grams of tissue).

20. The method according to claim 11, wherein one of the preselected second fluid flow or the preselected first fluid flow is from about 60 mL/min×100 g of tissue to about 100 mL/min×100 g of tissue (milliliters per minute per 100 grams of tissue).

21. A device for measuring capillary blood flow in absolute flow units, the device comprising:
a heater for applying heat to an area of skin to change the temperature of the skin from a first temperature to a second temperature and for maintaining a constant temperature gradient between the first and second temperatures, and a power source for providing power to the heater;
a temperature sensor for measuring temperature at the area of skin;
a controller in communication with the heater and the temperature sensor which operates the heater for maintaining the temperature gradient constant, and operates the temperature sensor in a first operative mode and a second operative mode, wherein
in the first operative mode the temperature sensor measures the first temperature at the area of skin,
and wherein in the second operative mode, the controller operates the heater to maintain the temperature gradient constant between the first and second temperatures;
a processor in communication with the controller for determining a capillary blood flow in absolute flow units corresponding to the measured first temperature and the heater power required to maintain the temperature gradient constant; and
a calibrating unit in communication with the processor which has been standardized in absolute flow units by:
in a wet model device, determining a first heater power dissipation corresponding to a preselected first fluid flow and determining a second heater power dissipation corresponding to a preselected second fluid flow, each in order to maintain the temperature gradient constant;
in a dry model device, adjusting the thermal conductivity of one or more layers at a first site on a first heat sink when the heater is operated at a first heater power obtained using the wet model device to obtain the constant temperature gradient in an adjusted dry model device at the preselected first fluid flow, and adjusting the thermal conductivity of one or more layers at a second site on a second heat sink when the heater is operated at a second heater power obtained using the wet model device to correspond to the constant temperature gradient in the adjusted dry model device at the preselected second fluid flow; and standardizing the calibrating unit in absolute flow units using the adjusted dry model device by assigning the first heater power to correspond to the preselected first fluid flow and assigning the second heater power to correspond to the preselected second fluid flow.

22. The device according to claim 21, wherein one of the preselected first fluid flow or the preselected second fluid flow is from about 1 mL/min×100 g of tissue to about 5 mL/min×100 g of tissue (milliliters per minute per 100 grams of tissue), or one of the preselected second fluid flow or the preselected first fluid flow is from about 60 mL/min×100 g of tissue to about 100 mL/min×100 g of tissue (milliliters per minute per 100 grams of tissue).

23. The device according to claim 21, wherein the heater for applying the constant temperature gradient comprises a first silicon diode or wherein the temperature sensor comprises a second silicon diode.

24. The device according to claim 21, wherein the heater comprises a first silicon diode, the temperature sensor comprises a second silicon diode, and the first and second silicon diodes are arranged in a diode array and are electrically insulated from each other.

25. The device according to claim 21, further comprising a display device in communication with the processor for visually displaying the measured capillary blood flow in absolute flow units.

26. The device according to claim 21, wherein the heater and the temperature sensor are combined into a capillary blood flow sensor module.

* * * * *